United States Patent
Mauchan et al.

(10) Patent No.: US 6,331,715 B1
(45) Date of Patent: Dec. 18, 2001

(54) DIAGNOSTIC ASSAY SYSTEM AND METHOD HAVING A LUMINESCENT READOUT SIGNAL

(75) Inventors: Donald E. Mauchan, Marlboro; Philip R. Norris, North Reading, both of MA (US)

(73) Assignee: Polaroid Corporation, Cambridge, MA (US)

(*) Notice: Subject to any disclaimer, the term of this patent is extended or adjusted under 35 U.S.C. 154(b) by 0 days.

(21) Appl. No.: 09/412,845

(22) Filed: Oct. 6, 1999

Related U.S. Application Data

(60) Provisional application No. 60/104,150, filed on Oct. 14, 1998.

(51) Int. Cl.[7] ..................................................... G01N 21/86
(52) U.S. Cl. .................................. 250/559.4; 250/559.02; 250/483.1; 422/52
(58) Field of Search ........................... 250/559.4, 559.02, 250/483.1, 484.2; 396/612; 422/52, 61, 102, 68.1, 87; 436/44, 46, 47, 172

(56) References Cited

U.S. PATENT DOCUMENTS

| | | | |
|---|---|---|---|
| 3,390,962 | 7/1968 | Goldsmith | 23/253 |
| 3,415,361 | 12/1968 | Adams, Jr. et al. | 206/47 |
| 3,680,967 | 8/1972 | Engelhardt | 356/246 |
| 3,788,205 | 1/1974 | Pasieka et al. | 95/93 |
| 3,865,548 | 2/1975 | Padawer | 23/230 |
| 4,111,754 | 9/1978 | Park | 195/127 |
| 4,233,029 | 11/1980 | Columbus | 23/230 |
| 4,254,083 | 3/1981 | Columbus | 422/55 |
| 4,264,560 | 4/1981 | Natelson | 422/58 |
| 4,271,119 | 6/1981 | Columbus | 422/50 |
| 4,302,313 | 11/1981 | Columbus | 204/195 R |
| 4,310,399 | 1/1982 | Columbus | 204/195 R |
| 4,323,536 | 4/1982 | Columbus | 422/56 |
| 4,371,498 | 2/1983 | Scordato et al. | 422/102 |
| 4,396,579 | 8/1983 | Schroeder et al. | 422/52 |
| 4,413,407 | 11/1983 | Columbus | 29/825 |
| 4,426,451 | 1/1984 | Columbus | 436/518 |
| 4,439,526 | 3/1984 | Columbus | 436/180 |
| 4,510,393 | 4/1985 | Sell et al. | 250/475 |
| 4,549,952 | 10/1985 | Columbus | 204/416 |
| 4,587,221 | 5/1986 | Cais et al. | 436/500 |
| 4,608,231 | 8/1986 | Witty et al. | 422/61 |
| 4,675,299 | 6/1987 | Witty et al. | 436/165 |
| 4,757,004 | 7/1988 | Houts et al. | 435/7 |
| 4,772,453 | 9/1988 | Lisenbee | 422/52 |
| 4,797,259 | 1/1989 | Matkovich et al. | 422/101 |
| 4,833,087 | 5/1989 | Hinckley | 435/287 |
| 4,863,689 | 9/1989 | Leong et al. | 422/52 |
| 4,906,439 | 3/1990 | Grenner | 422/56 |
| 4,918,025 | 4/1990 | Grenner | 436/165 |
| 4,948,564 | 8/1990 | Root et al. | 422/101 |
| 4,948,975 | 8/1990 | Erwin et al. | 250/361 |
| 4,959,324 | 9/1990 | Ramel et al. | 436/169 |
| 4,973,549 | 11/1990 | Khanna et al. | 435/11 |
| 4,978,502 | 12/1990 | Dole et al. | 422/58 |
| 4,985,631 | 1/1991 | Wannlund et al. | 250/361 |
| 4,987,085 | 1/1991 | Allen et al. | 324/407 |
| 5,011,663 | 4/1991 | Innocenti | 422/102 |

(List continued on next page.)

FOREIGN PATENT DOCUMENTS

WO 97/27463   7/1997   (WO).

Primary Examiner—Que T. Le
(74) Attorney, Agent, or Firm—Paul M. Coryea

(57) ABSTRACT

The present invention provides a method of providing a self-contained processor having a luminescent testing material capable of generating a read-out signal in response to contact with a reagent of interest in a test sample. In an alternate aspect, the present invention also provides a portable and self-contained diagnostic assay system for detecting and recording the presence of a luminescent signal generated by a reaction between a luminescent testing material and a reagent in a test sample on a self-developing film assemblage.

18 Claims, 3 Drawing Sheets

U.S. PATENT DOCUMENTS

| | | | |
|---|---|---|---|
| 5,035,866 | 7/1991 | Wannlund | 422/102 |
| 5,063,090 | 11/1991 | Wannlund | 427/384 |
| 5,073,484 | 12/1991 | Swanson et al. | 435/7.92 |
| 5,075,077 | 12/1991 | Durley, III et al. | 422/56 |
| 5,093,268 | 3/1992 | Leventis et al. | 436/172 |
| 5,098,661 | 3/1992 | Froehlich et al. | 422/102 |
| 5,100,621 | 3/1992 | Berke et al. | 422/61 |
| 5,132,086 | 7/1992 | Allen et al. | 422/56 |
| 5,159,197 | 10/1992 | Wannlund | 250/328 |
| 5,164,301 | 11/1992 | Thompson et al. | 435/29 |
| 5,167,922 | 12/1992 | Long | 422/58 |
| 5,188,965 | 2/1993 | Wannlund | 436/165 |
| 5,219,762 | 6/1993 | Katamine et al. | 436/518 |
| 5,244,630 | 9/1993 | Khalil et al. | 422/52 |
| 5,319,436 | 6/1994 | Manns et al. | 356/246 |
| 5,332,549 | 7/1994 | MacIndoe, Jr. | 422/63 |
| 5,355,215 | 10/1994 | Schroeder et al. | 356/317 |
| 5,411,893 | 5/1995 | Eden et al. | 436/165 |
| 5,418,171 | 5/1995 | Kimura et al. | 436/518 |
| 5,441,894 | 8/1995 | Coleman et al. | 436/518 |
| 5,457,527 | 10/1995 | Manns et al. | 356/246 |
| 5,460,778 | 10/1995 | Macindoe, Jr. | 422/63 |
| 5,482,839 | 1/1996 | Ashihara et al. | 435/7.9 |
| 5,552,276 | 9/1996 | Mochida | 435/6 |
| 5,657,118 | 8/1997 | Lee | 356/246 |
| 5,783,399 * | 7/1998 | Childs et al. | 435/7.2 |

* cited by examiner

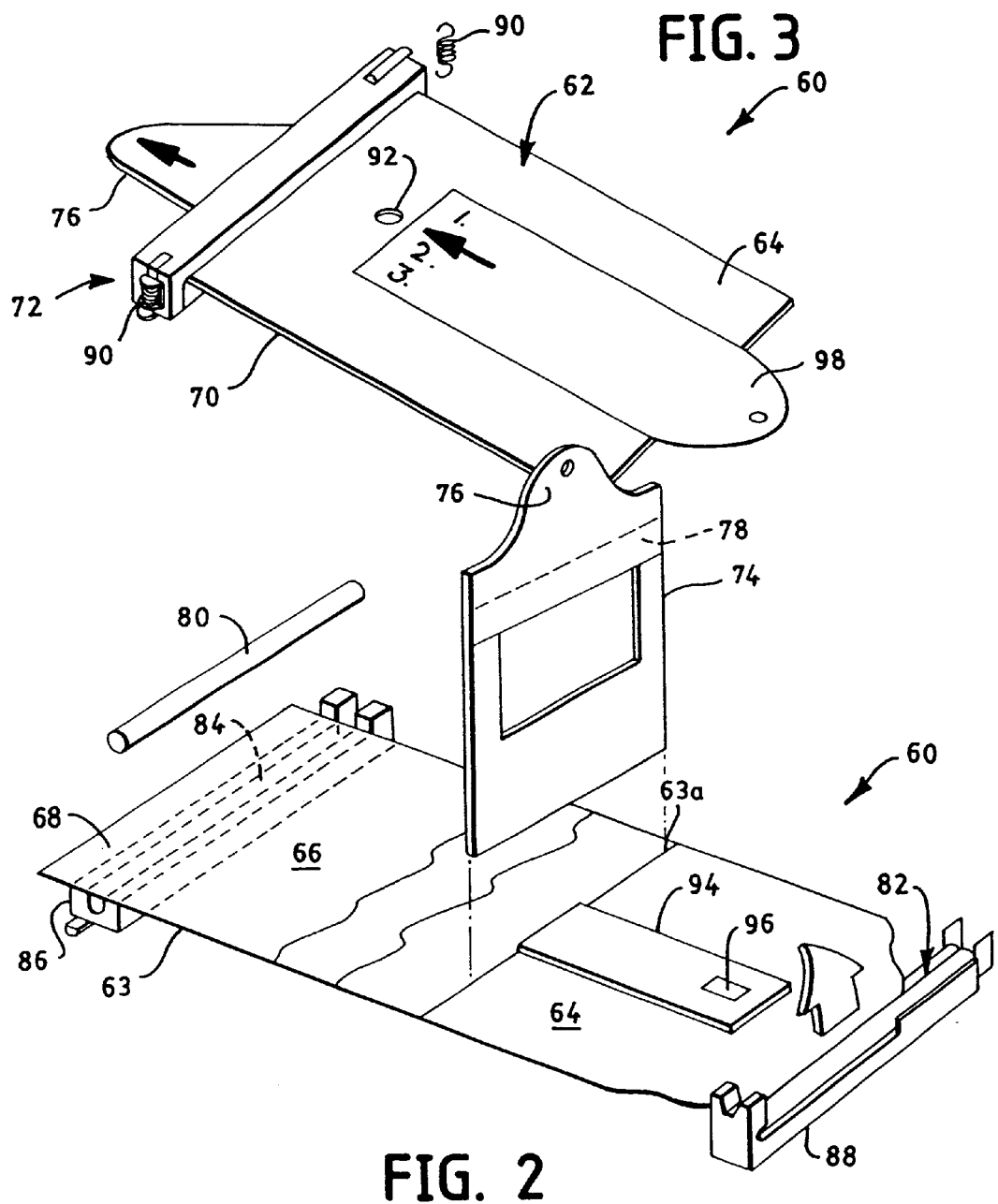

DIAGNOSTIC ASSAY SYSTEM AND METHOD HAVING A LUMINESCENT READOUT SIGNAL

CROSS-REFERENCE TO RELATED APPLICATIONS

The present application is a non-provisional patent application, filed Oct. 14, 1998 and having Ser. No. 60/104,150 and is related to non-provisional patent application Ser. No. 09/417,297 entitled "Method and Apparatus for Performing Diagnostic Testing" filed concurrently herewith.

BACKGROUND OF THE INVENTION

The present invention relates generally to diagnostic assay systems and methods and, in particular, diagnostic assay systems and methods for recording luminescent activities on image recording material in a reliable and economical manner.

Recording the occurrence of luminescent reactions, such as of the chemiluminescent type for qualitative and quantitative results on image recording devices is well known in the diagnostic assay art. A class of analytical instruments referred to as luminometers are typically used to conduct and record luminescent reactions of, for instance, a biological fluid containing a reagent of interest, such as an analyte, and a reagent in an assay element. Examples of these approaches include single-sample luminometers fitted with photographic multipliers; single-sample luminometers fitted with solid-state detectors; multiple sample luminometers; automatic luminometers fitted with imaging systems based on CCD cameras; and photographic camera luminometers. Devices using photographic films of the conventional and self-developing type for recording luminescent activity are described in, for example, in U.S. Pat. Nos.: 4,863,689; and 5,035,866. Heretofore known prior art in this field tends to be limited in a number of ways, such as being expensive due to among other factors expensive electronics, requiring relatively significant training in order to operate and being relatively cumbersome in construction and/or use.

Despite the existence of a wide variety of known diagnostic luminescent type testing systems and approaches, however, it is, nevertheless, desired to improve upon the overall ease, versatility, and reliability of such systems and their testing procedures, as well as reduce overall costs associated with their construction and use.

SUMMARY OF THE INVENTION

In accordance with the present invention, provision is made for a method of detecting and recording the presence of a luminescent activity. The method includes the steps of: providing a self-contained processor having a luminescent testing material capable of generating a read-out luminescent signal recordable on image recording material in response to contact with a reagent of interest in a test sample; providing a film assemblage of the self-developing type having a portion to be exposed and a leader extending from the processor; introducing the test sample into the processor so as that a reagent of interest can cooperate with the test material; exposing the exposable portion of the self-developing film unit retained in a light-tight enclosure in the processor to a luminescent reaction of the reagent of interest and the test material; and, initiating development of the exposed portion by passing it through pressure applying processing means in the processor and withdrawing the exposed portion from the enclosure by pulling on the film leader.

In another illustrated embodiment, there is provided a method of detecting and recording the presence of a reagent in a sample of test fluid. Included is the steps of providing a self-contained processor having a luminescent testing assembly in a light-tight enclosure capable of generating a luminescent signal in response to presence of a reagent in a test fluid sample; introducing a test sample fluid through a port in the processor; transporting the fluid sample to a luminescent testing assembly within the processor for generating a luminescent signal if the reagent is present; exposing a portion of a self-developing film unit retained in a light-tight portion of the processor to the luminescent signal; and, initiating development of the exposed portion by pulling on an extension portion of the film unit protruding from the processor, whereby the exposed portion passes from the light-tight portion to pressure applying processing means in the processor.

Yet another embodiment includes a method of detecting and recording the presence of a reagent in a test sample; wherein the method comprises the steps of providing a self-contained processor having a luminescent testing material in a light-tight enclosure capable of generating a luminescent signal in response to presence of a reagent in a test sample; introducing a probe into contact with the testing material; said introducing step including the step of penetrating a light-tight sealing member in the processor prior by the probe; exposing a portion of a self-developing film unit retained in a light-tight portion of the processor to the luminescent signal if the reagent is present on the probe by passing the signal through a transparent wall portion of the enclosure which can expose the film portion to the signal; and, initiating development of the exposed portion by pulling on an extension portion of the film unit protruding from the processor, whereby the exposed portion passes from the light-tight portion to pressure applying processing means in the processor.

In another embodiment, provision is made for transporting the sample fluid by inducing capillary flow thereof. In such embodiment, the capillary flow is conducted in a light-tight manner.

In another embodiment, provision is made for transporting the sample fluid by capillary action carried out by providing an opaque, biologically inert and porous assembly which is interposed between the port and the luminescent testing material.

Another illustrated embodiment includes a diagnostic assay system for detecting and recording the presence of a luminescent signal generated in a manner noted above. The system comprises a processor housing assembly for containing a luminescent testing material capable of generating a luminescent signal in response to contact with a reagent in a test sample. Included is means for introducing the test sample into the processor so as to cooperate with the test material; as well as means for exposing the exposable portion to a luminescent signal. The system includes processing means in the processor housing assembly for allowing the exposed portion to pass therethrough so as to initiate development of the exposed portion in response to pulling on an extension portion and withdrawing the exposed portion from the enclosure.

In another illustrated preferred embodiment, provision is made for a diagnostic processor apparatus. The apparatus includes a housing assembly having a film assemblage therein, preferably of the self-developing type. A reservoir containing fluid is retained within the housing assembly that is a solution carrying a reagent capable of generating a luminescent activity when in the presence of a reagent of interest that is found in a test sample. Provision is made for means for transferring a light signal to the film assemblage. Means are provided for sealing the fluid in the reservoir and are operable for allowing introduction of a test sample member carrying a test sample to be tested into the reservoir.

In an illustrated embodiment, the sealing means includes a penetrable membrane. Also, provision is made for a test sample member that penetrates the sealing means and enters the reservoir with a reagent of interest. Light-shielding means on the test sample member prevents ambient light from entering the reservoir and, thereby striking the film after the test sample penetrates the sealing membrane.

It is an object of the present invention to provide an improved method and system for conducting and recording luminescent reactions, wherein the results are immediately and reliably made known to an operator and permanently recorded.

It is another object of the present invention to provide an improved method and system for conducting and recording luminescent reactions in a hand-held assay processor using self-developing type film.

It is another object of the present invention to provide an improved method and system for providing a platform wherein the film can be loaded during assembling.

It is another object of the present invention to provide an improved method and system for conducting and recording luminescent reactions in a hand-held assay processor that is disposable after single use.

It is another object of the present invention to provide for an improved method and system which is simple and reliable to operate and which is low-cost in construction.

The above and other objects and features of the present invention will become apparent when reading the following description taken conjunction with the accompanying drawings wherein like parts are indicated by like reference numerals throughout the several views.

BRIEF DESCRIPTION OF THE DRAWINGS

FIG. 2 is an exploded perspective view of another embodiment of the present invention that is similar to that illustrated in FIG. 1;

FIG. 3 is a perspective view illustrating the components of FIG. 2 in an assembled condition; and, FIG. 4 is a schematic view of still another embodiment of the present invention.

DETAILED DESCRIPTION

Figure 1:
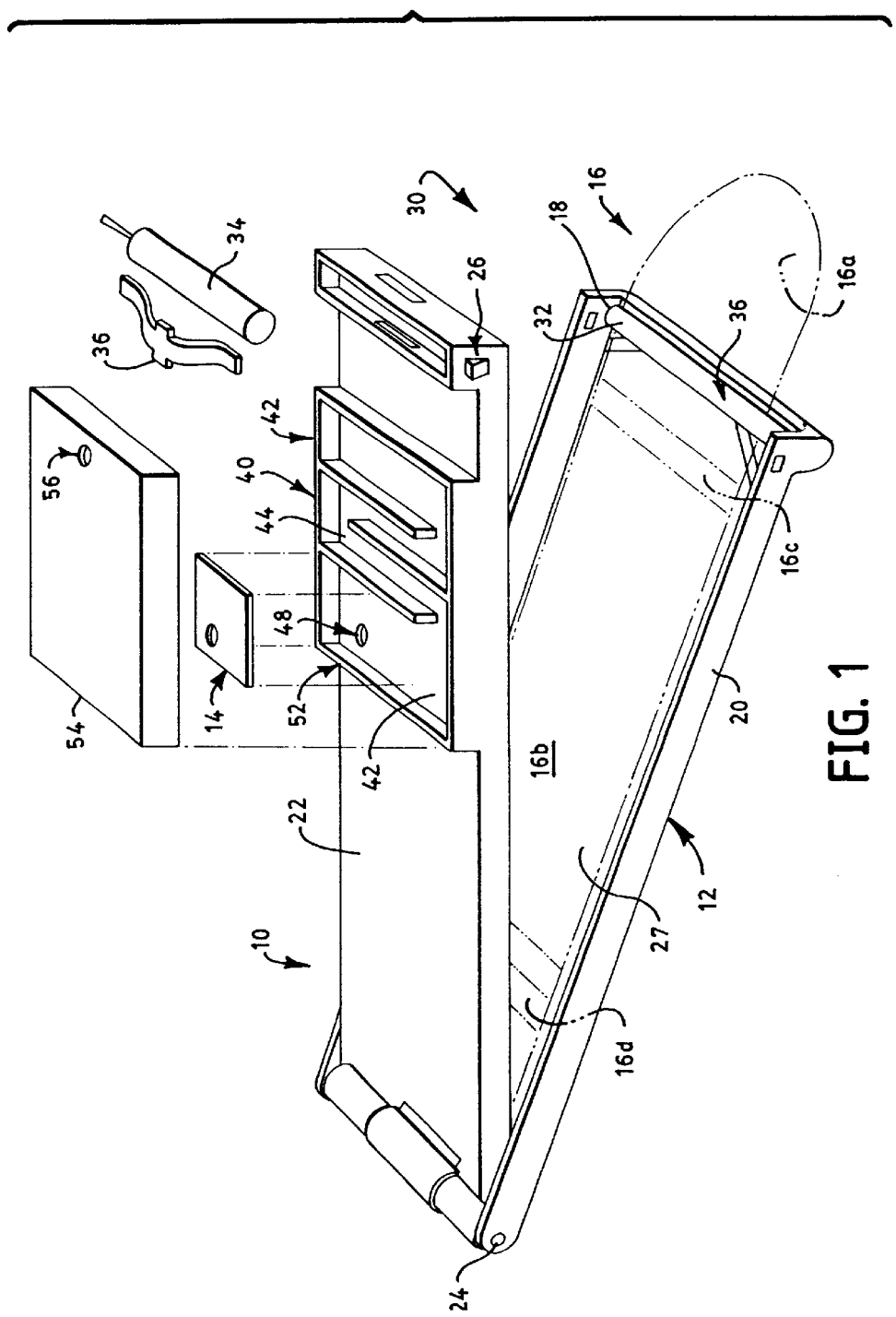
FIG. 1 is an exploded perspective view illustrating major components forming one embodiment of an improved diagnostic assay system made according to the present invention.

Reference is made to FIG. 1 for illustrating an improved self-contained, and portable diagnostic assay system 10 made in accordance with the principles of the present invention, wherein the presence of a reagent in a test sample can be detected by its interaction with an assay element that generates a luminescent signal that is recorded permanently on imaging media.

In the first illustrated preferred embodiment, the self-contained assay system 10 includes a portable, hand-held processor housing assembly 12; a biological assay element in the form of a rectangular test strip 14; and, a film assemblage 16; preferably, of the integral self-developing type. The assay element can be any type that generates a read-out signal of the luminescent signal capable of being recorded on a photographic film in response to being in contact with a reagent of interest, such as an analyte, found in a test sample of fluid. The terms "luminescent signal or read-out signal" in the specification and claims is understood to include any signals, such as chemiluminescent, fluorescent, infrared, etc. that are recordable on image recording material. The present invention envisions that a variety of assay elements can be used that are selected to interact with a particular reagent of interest. Other kinds of image recording materials are contemplated, such as for instance, conventional 35-mm photographic film. Both the test strip and film unit are preloaded into the housing assembly, although they can be preloaded at different times, as will become apparent in the following description.

The film assemblage 16 is adapted to be exposed and processed within the processor housing assembly 12 for developing any latent luminescent images in a manner to be described. It should be noted that the construction of the film assemblage 16 is similar in construction to the film assemblage described and illustrated in copending and commonly-assigned U.S. patent application Ser. No. 08/829,914, filed in the U.S. Patent and Trademark Office on Mar. 4, 1997, now U.S. Pat. No. 5,848,316; which description is incorporated herein as a part hereof. Since the test strip and the film assemblage 16 do not, per se, form an aspect of the present invention, only those details thereof necessary for understanding the present invention will be set forth. Basically, the film assemblage 16 is an elongated assembly having a leader portion 16a, an image recording area 16b, a pod 16c of processing fluid located at a leading end portion, and a fluid trap 16d at a trailing end. The photosensitive image recording area 16b is positioned within the housing assembly so as to be exposed to any luminescent activity that may be generated by a particular reagent in a test sample interacting with the reagent in the test strip. The pod 16c is positioned adjacent the processing means, as will be described and the leader portion 16a protrudes from the film exit 18 so that it may be manually grasped for pulling and processing of the film unit. The film exit is appropriately provided with flaps (not shown) or the like for providing a light-tight enclosure.

In the illustrated embodiment, the processor housing assembly 12 includes a pair of generally rectangular and matable lower and upper plate-like processor housing portions 20 and 22. The housing portions are hingedly connected as at 24 at a trailing end thereof, and releasably latched as at 26 at a forward end thereof. The housing assembly 12 is, preferably, dimensioned to be hand-held and portable for convenience in use. The housing portions 20 and 22 can be made of any material suitable to define, preferably, a light-tight enclosure 27 for housing the image recording area 16b. While a hinged coupling is described, a wide variety of approaches can be used for joining the two opposed housing components are envisioned. The lower processor housing portion 20 is similar in construction to that described in the last-noted application and basically includes a film supporting wall 28, a processing fluid spreading structure 30 for spreading the processing fluid ruptured from the pod in a well-known manner. A lower spread roller 32 is rotatably supported in the lower housing portion 20 for cooperating with a biased upper spread roller 34 in the upper housing portion 22 to define a pressure nip. The rollers 32 and 34 serve to rupture the pod and spread the processing fluid as a film unit passes therethrough. In addition, the nip acts to inexpensively retain the film assemblage 16 within the housing prior to use of the device. Accordingly, the film can be transported and handled without fear of it becoming dislodged or otherwise separated. The upper spread roller 34 is retained in a well and is biased by a leaf spring 36 for providing the necessary resilient biasing force for facilitating pod rupturing spreading of the processing fluid, thereby initiating development of latent images.

Since this embodiment is intended to be a so-called disposable unit, the film must be protected as it is loaded into the processor housing assembly.

In this embodiment, the upper housing portion 22 is provided with a, preferably, molded grooved arrangement 40 on an interior surface thereof that defines a generally rectangular test strip receiving well 42. The receiving well 42 is in fluid communication with a capillary type fluid delivery channel 44 that is, in turn, in fluid communication with test fluid reservoir 46. The reservoir 46 is for receiving a biological test fluid introduced therein by any suitable means, such as a pipette; not forming a part of this invention. A light transmitting aperture 48 in the well 42 is in optical communication with the image recording area 16*b*, after the dark slide 38 has been removed. A suitably dimensioned chemiluminescent testing assembly or assay test strip 14 is to loaded in the well 42 for interaction with a preselected reagent, such as an analyte. The analyte is carried in a biological fluid test sample that is delivered to the reservoir and from the reservoir via the fluid delivery channel 44 to the test strip. The test assembly or test strip 14 can be constructed from any of a wide variety of materials so long as it generates a luminescent signal capable of being recorded on film in response to interacting with a reagent carried in the test fluid. The capillary delivery channel 44 is comprised of a labyrinth grooved construction that is molded in the upper surface and serves to transfer the test fluid sample from the reservoir to the well by virtue of capillary action. Therefore, it will be appreciated that the delivery channel 44 is constructed and dimensioned to induce or allow capillary action to transfer the test fluid from the reservoir to the well. In this embodiment, the walls 52 defining the delivery channel 44 have a depth in the order of about 0.005 inch to 0.0025 inch in order to transfer the fluid by virtue of capillary action. The fluid reservoir 46 is of sufficient size to accommodate the quantity of test fluid to be deposited therein and, as noted, is in fluid communication with the channel 44. A rectangular cover 54 having a fluid reservoir opening 56 is placed in covering relationship to the grooved arrangement 40. The cover 54 is suitably joined, as by heat bonding or adhesives, to the upper portion 22. The fluid opening 56 is in direct fluid communication with the reservoir 46 so as to allow delivery of the test fluid, as by a pipette, to the reservoir. The cover 54 can, if desired, be removably joined to the upper housing portion should it be so desired. In addition to the capillary action provided by the channels, the present invention contemplates that use of a wicking device made of suitable material (not shown) that can be added to the channel 44 to assist in transferring the test fluid. It is equally clear that the present invention envisions substituting a wicking system for the capillary channel itself. While one particular molded arrangement is illustrated for effecting the capillary flow, a wide variety of configurations and dimensions can be used for transferring the fluid. It is further envisioned other than liquid actuated systems are contemplated, such as gaseous mediums.

After explaining the construction, the operation thereof is self-evident. However, the following brief description of the operation is provided as a supplement. An operator introduces a test fluid sample through the reservoir opening 56, as by a pipette, into the reservoir. The test fluid sample is transferred by reason of the capillary action induced by the capillary channel 44 to the test strip 14. If the test fluid contains the analyte which is being tested for by the test strip 14, a chemiluminescent reaction will, after a prescribed period of time, occur. The generated signal will be transmitted to the film through the opening and is recordable on the image recording area 16*c*. It will be further appreciated, as noted, that prior to the test being performed, the dark slide 38 is removed to allow the luminescent activity to expose the film and thereby permanently record the test. To process the film, the protruding tab 16*a* is pulled after a prescribed period of time, for example sixty (60) seconds. Any kind of suitable timing mechanism can be provided to achieve the timing, such as a timer independent of the device or one that is combined therewith (not shown). As noted, the pressure applying rollers rupture the pod 16*c* and spread the fluid to develop any latent image generated by the chemiluminescence. For instance, the test will indicate either a positive or negative result in a manner that is quickly and easily ascertained. The result is simple to read and understand and is one that does not require user interpretation, such as determining the color of a test result or calculating any quantification. It will be appreciated that as a consequence, a safe and simple diagnostic test is performed that provides a positive record of the test being conducted. Such testing is of particular benefit, particularly in the home testing market wherein it can be used for a variety of diagnostic tests with a certainty of results and a significant ease of operation.

Reference is made to FIGS. 2 and 3 for another preferred embodiment of a processor 60 in which the processor housing assembly 62 is made of an elongate and opaque sheet 63 made of a suitable flexible and opaque material, such as plastic or paper that can be folded along a fold line 63*a* to define a pair of generally coextensive upper and lower panels 64, 66. The panels 64 and 66 are sealed along opposite marginal ends and have an open mouth 68 to define a light-tight pouch or enclosure 70. The leading ends of the panels adjacent the open mouth 68 are attached to a processing assembly 72 which assists in providing a light-tight enclosure.

Figure 4:
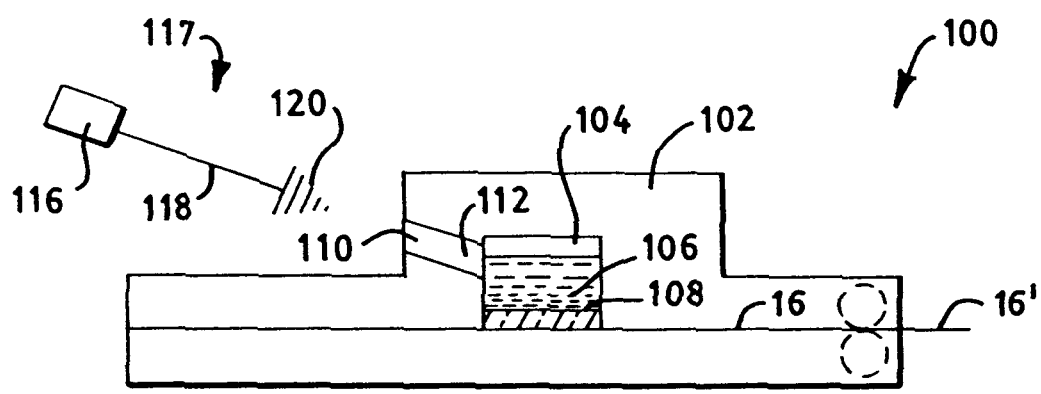

Sandwiched between the panels 64, 66 is a generally rectangular strip of self-developing film 74 of the integral type; such as described in the last noted embodiment. A pull tab 76 is attached to a leading end of the film 74 and protrudes from the open mouth 68 through the processing assembly 72. Indicia is printed on the tab 76 to provide instructions for an operator. A pod 78 of processing fluid is provided on the film unit so as to be disposed inwardly of a pair of lower and upper pressure applying spread rollers 80, 82 of the film processing assembly 72. One end of the panel 66 extends over an elongated groove 84 in a lower plastic cradle 86 and is assisted in being secured thereto by the lower spread roller 80. Likewise, a leading end of the panel 64 extends over an elongated groove (not shown) in an upper plastic cradle 88. A pair of springs 90 at opposite longitudinal ends of the cradles act to provide the latter with the necessary resilient biasing force for holding the film within the light-tight enclosure 70 and securing a generally light-tight arrangement about the mouth 68. A fluid port 92 is provided in the upper panel for allowing a test fluid sample to be delivered to an elongated fluid capillary strip 94. The capillary strip 94 is secured, as by adhesives, to an interior surface of the upper panel 64. The strip 94 is generally opaque to ambient light to provide further light-tight features of the processor. In addition, the strip 94 is preferred to be biologically inert, light-tight and is, of course, suitably porous to induce capillary flow. The material can be, for instance, an iron oxide fibrous mesh pad or other porous membrane that will allow capillary flow and which will not interact with the reagent being tested for in the sample fluid. It is interposed between the port and the luminescent testing material. Examples of the materials that the strip can be made from include polypropylene, polyethylene base materials having iron oxide in combination therewith. A luminescent assay test strip or patch 96 that can be of any suitable type that generate a luminescent, fluorescent signal in response to reacting with a particular analyte in the test fluid sample. One end of the strip 94 is positioned beneath the port 92 so as to receive and transfer the sample fluid deposited thereon to the test patch located within the enclosure. Accordingly, if the test fluid contains the particular analyte or reagent in the test sample, a luminescent activity is generated on the patch that is sufficient in strength to expose the film unit in juxtaposed relationship therewith. The resulting latent image can be processed in a similar manner as described above in connection with the above embodiment. Basically, the tab or leader 76 is pulled and the film unit is pulled from the processor housing. The pod is ruptured and the resulting processing fluid is spread over the latent image for processing of the same. A hold tab 98 is secured to the upper panel 64, longitudinally opposite the tab or leader 76, whereby a user can hold the tab 98 in order to facilitate the pulling of the tab 76. The hold tab 98 can also be provided with indicia for a variety of reasons. Reference is made to FIG. 4 for illustrating a schematic of another embodiment of the present invention, wherein a single or disposable diagnostic assay device 100 is depicted. This embodiment is similar to that described in FIG. 1 and thus similar structure will be represented by similar reference numerals with, however, the addition of prime markings. Instead of the upper housing portion 22' being provided with the molded capillary construction as in FIG. 1, there is, instead provided a generally parallelepiped housing assembly 102 providing a reservoir 104 for containing a preselected testing fluid 106. A transparent window 108 defines a bottom wall of the reservoir and is juxtaposed to the film 16'; whereby generation of a chemiluminescent activity within the fluid will expose the film therethrough. A passageway 110 is formed in the housing assembly 102 and leads from the exterior thereof to the reservoir 104. A light-tight, metallic sealing membrane 112 is positioned within the passageway 110 in juxtaposed relationship to the reservoir. The sealing membrane 112 is for fluid-tight sealing of the fluid 106 within the reservoir and also for preventing contamination of such fluid as well as preventing ambient light into the reservoir which otherwise might expose the film. The passageway 110 has a cross-sectional dimension that snuggly accommodates a testing sample pick-up 114 and which forms a light-tight arrangement. The sample pick-up 114 includes a handle 116, a stem 118 and sampling rings 120. The fluid 106 can be one that generates a chemiluminescent signal in response to a reagent, such as ATP (Adenosine Triphosphate) being present on the sampling rings. ATP is used as an indicator of the presence of organic debris, such as microorganisms. The fluid 106 can be, for example, a Firefly reagent which generates a light signal in response to ATP collected on the sampling rings. The sample pick-up 114, the fluid 106 and the membrane 112 can like that available from Biotrace, Inc., New Jersey. It is of course, realized that the present invention contemplates use of a wide variety of fluids, membranes and sample pick-ups that can be used in the device of the present invention. The foregoing materials provide but some of the many which can be used in the context of the present invention.

In operation, the sample pick-up, after touching a surface to be tested for microorganisms is inserted into the passageway 110 and the reservoir 104. During the insertion step, the sampling rings portion punctures the sealing membrane 112. If the sampling rings contain ATP, for instance, the reagents in the fluid 106 will generate a chemiluminescent signal, after a predetermined time. The signal generated exposes the film 16' through the window 108. To process the latent images of such a signal on the film, the operator merely pulls on the tab extending from the processor housing assembly so that the film is processed as described above. Thereafter, diagnostic assay system is disposed. Accordingly, there is provided a unique and simplified approach for rapidly and accurately testing surfaces for microorganisms and providing a permanent record of the test. The film system is versatile and allows written indicia to be recorded on the film assemblage so as to assist in record keeping.

Although the foregoing invention has been described in some detail, it will be readily apparent to those of ordinary skill in the art that certain changes and modifications may be made thereto without departing from the spirit and scope of the appended claims.

What is claimed is:

1. The method includes the steps of: providing a self-contained processor having a luminescent testing material capable of generating a read-out signal in response to contact with a reagent of interest in a test sample; providing a film assemblage of the self-developing type having a portion to be exposed and a leader extending from the processor; introducing the test sample into the processor so as that a reagent of interest can cooperate with the test material; exposing the exposable portion of the self-developing film type retained in a light-tight enclosure in the processor to a luminescent reaction of the reagent of interest and the test material; and, initiating development of the exposed portion by passing the exposable portion through pressure applying processing means in the processor and withdrawing the exposed portion from the enclosure by pulling on the film leader.

2. A method of detecting and recording the presence of a reagent in a sample of test fluid; said method comprising the steps of: providing a self-contained processor having a luminescent testing assembly in a light-tight enclosure capable of generating a luminescent read-out signal in response to presence of a reagent in a test fluid sample; introducing a test sample fluid through a port in the processor; transporting the fluid sample to the luminescent testing assembly within the processor for generating a luminescent signal if the reagent is present; exposing a portion of a self-developing film unit retained in a light-tight portion of the processor to the luminescent signal; and, initiating development of the exposed portion by pulling on an extension portion of the film unit protruding from the processor, whereby the exposed portion passes from the light-tight portion to pressure applying processing means in the processor.

3. A method of detecting and recording the presence of a reagent in a test sample; said method comprising the steps of: providing a self-contained processor having a luminescent testing material in a light-tight enclosure capable of generating a luminescent read-out signal in response to presence of a reagent in a test sample; introducing a probe into contact with the testing material; said introducing step including the step of penetrating a light-tight sealing member in the processor prior by the probe; exposing a portion of a self-developing film unit retained in a light-tight portion of the processor to the luminescent signal if the reagent is present on the probe by passing the signal through a transparent wall portion of the enclosure which can expose the film portion to the signal; and, initiating development of the exposed portion by pulling on an extension portion of the film unit protruding from the processor, whereby the exposed portion passes from the light-tight portion to pressure applying processing means in the processor.

4. The method of claim 2 wherein the step of transporting the sample fluid includes utilizing capillary flow.

5. The method of claim 4 wherein the capillary flow is conducted in a light-tight manner.

6. The method of claim of 5 wherein the step of transporting the sample fluid is carried out by a molded labyrinth internal of the processor.

7. The method of claim 4 wherein the step of transporting the sample fluid is by capillary action carried out by providing an opaque, biologically inert and porous assembly which is interposed between the port and the luminescent testing material.

8. A portable and self-contained diagnostic assay system for detecting and recording the presence of a luminescent signal generated by a reaction between a luminescent testing material and a reagent in a test sample on a self-developing film assemblage including a strip of self-developing film having a single exposable area with a light-tight enclosure; said system comprises: a portable and self-contained processor housing assembly for containing a luminescent testing material capable of generating a luminescent read-out signal in response to contact with a reagent in a test sample; means for introducing the test sample in to the processor so as to cooperate with the test material; means for exposing the exposable area to a luminescent signal; and, processing means in the processor housing assembly for allowing the exposed portion to pass therethrough so as to initiate development of the exposed portion in response to pulling on an extension portion and withdrawing the exposed portion from the enclosure.

9. A portable and self-contained diagnostic assay system for detecting and recording the presence of a luminescent test sample signal generated by a reaction between a luminescent testing material and a reagent in a test sample; said system comprises: a processor housing assembly for containing a luminescent testing material capable of generating a luminescent signal in response to contact with a reagent in a test sample; a luminescent testing material in a housing assembly capable of generating a luminescent test sample signal in response to contact with a reagent in the test sample; a self-developing film assemblage including a strip of self-developing film having a single exposable portion within a light-tight enclosure in the housing assembly, a leading end portion of the film strip extends from an exit in the housing assembly for allowing a user to withdraw the film from the housing assembly in response to pulling of the leading portion; means for introducing the test sample into the processor so as to cooperate with the test material; means for exposing the exposable portion to a test sample signal; and, processing means in the processor housing assembly for allowing the exposed portion to pass therethrough so as to initiate development of the exposed portion in response to pulling of the leading end portion whereby the film is withdrawn from the enclosure.

10. The system of claim 9 wherein the means for introducing the sample fluid includes means for effecting capillary flow.

11. The system of claim 10 wherein the means for effecting capillary flow is conducted by a labyrinth passageway, which is, molded internally of the processor and effects a light-tight relationship.

12. The system of claim 10 wherein the means for effecting capillary flow is an opaque, biologically inert and porous assembly that is interposed between a fluid inlet port in the housing assembly and the luminescent testing material.

13. A diagnostic processor apparatus comprising: a housing assembly having a film assemblage therein, a reservoir which can contain a fluid is retained within the housing assembly which fluid is a solution carrying a reagent capable of generating a luminescent read-out signal activity when in the presence of a reagent of interest that is found in a test sample; means for transferring a light signal to the film assemblage; and, means is provided for sealing the fluid in the reservoir and is operable for allowing introduction of a test sample member carrying a test sample to be tested into the reservoir.

14. The processor according to claim 13, wherein the sealing means includes a penetrable membrane.

15. The processor according to claim 14, further including a test sample member that penetrates the sealing means and enters the reservoir with a reagent of interest.

16. The processor according to claim 14, further including light-shielding means on the test sample member for preventing ambient light from entering the reservoir and, thereby striking the film after the test sample penetrates the sealing membrane.

17. The processor according to claim 14, wherein reservoir includes a transparent window in juxtaposed relationship to the film for exposing the latter.

18. The processor according to claim 13, wherein processor housing has a construction allowing it to be held and portable.

* * * * *